(12) United States Patent
Wong et al.

(10) Patent No.: US 9,678,000 B1
(45) Date of Patent: *Jun. 13, 2017

(54) REDUCTION OF SCATTERING NOISE WHEN USING NDIR WITH A LIQUID SAMPLE

(71) Applicant: Airware, Inc., Goleta, CA (US)

(72) Inventors: Jacob Y Wong, Goleta, CA (US); Thomas Campbell, Newbury Park, CA (US)

(73) Assignee: AIRWARE, INC., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/444,136

(22) Filed: Feb. 27, 2017

Related U.S. Application Data

(63) Continuation-in-part of application No. 15/358,873, filed on Nov. 22, 2016, now Pat. No. 9,606,053.

(51) Int. Cl.
*G01N 33/49* (2006.01)
*G01N 21/3504* (2014.01)

(52) U.S. Cl.
CPC ......... *G01N 21/3504* (2013.01); *G01N 33/49* (2013.01)

(58) Field of Classification Search
CPC .......................... G01N 21/3504; G01N 33/49
See application file for complete search history.

(56) References Cited

U.S. PATENT DOCUMENTS

| | | | | |
|---|---|---|---|---|
| 5,077,469 A | * | 12/1991 | Fabinski | G01N 21/274 250/343 |
| 6,509,567 B2 | * | 1/2003 | Boudet | G01M 3/002 250/343 |
| 2007/0017458 A1 | * | 1/2007 | Frodl | G01N 21/3504 122/379 |
| 2014/0266748 A1 | * | 9/2014 | Wong | G08B 21/12 340/632 |
| 2015/0129767 A1 | * | 5/2015 | Kouznetsov | G01N 21/0303 250/341.1 |
| 2015/0129770 A1 | * | 5/2015 | Henderson | G01N 21/3504 250/343 |
| 2016/0178508 A1 | * | 6/2016 | Ramsteiner | G01N 21/31 356/432 |

* cited by examiner

*Primary Examiner* — Mark R Gaworecki
(74) *Attorney, Agent, or Firm* — Roy L. Anderson

(57) ABSTRACT

A concentration of glucose in a blood sample is determined through use of a signal channel output/reference channel ratio obtained by use of an NDIR absorption technique in which scattering noise attributable to the liquid phase is reduced by alternately and successively pulsing infrared radiation from signal and reference sources which are multiplexed and collimated into a pulsed beam directed through the sample space containing the liquid phase and the pulse frequency is sufficiently fast so that a given molecule of glucose will not pass in and out of the sample space within the pulse frequency.

4 Claims, 6 Drawing Sheets

REDUCTION OF SCATTERING NOISE WHEN USING NDIR WITH A LIQUID SAMPLE

CROSS-REFERENCE TO RELATED APPLICATIONS

The present invention is a continuation-in-part application which claims priority from U.S. Ser. No. 15/358,873, filed Nov. 22, 2016, the disclosure of which is specifically incorporated herein by reference.

FIELD OF THE INVENTION

The present invention relates to scattering noise reduction in the measurement of particles in liquid via Non-Dispersive Infra-Red (NDIR) technique.

BACKGROUND OF THE INVENTION

Non-Dispersive Infra-Red (NDIR) is a common measurement principle for detecting gases in the environment. NDIR sensors utilize the principle that various gases exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating, for isolating for the purpose of measurement the radiation in a particular wavelength band that coincides with a strong absorption band of a gas to be measured.

NDIR has enjoyed widespread use in gas measurement because NDIR gas sensors are highly accurate, relatively stable and easy to operate and maintain.

The present invention is concerned with addressing problems arising from use of NDIR to detect molecules in a liquid medium, rather than in gas.

SUMMARY OF THE INVENTION

The present invention is generally directed to a process and apparatus useful for determining a sample concentration of a chosen molecule in a liquid phase in which infrared radiation from a signal source and a reference source are alternately and sequentially pulsed at a frequency of N Hz (preferably 10 KHz or greater with a duty factor around 20-25%) into a multiplexer and collimated into a pulsed beam which is directed through a sample space containing the liquid phase. A detector detects infrared radiation as a pulsed signal after it passes through the liquid phase and signal processing electronics is used to obtain an average ratio value of $R_{ave}(t)$ for a preselected period of time ("t") from the pulsed signal and reference channel output, where $R_{ave}(t)$=signal channel output/reference channel output for the preselected period of time, which is then used to calculate the sample concentration of the chosen molecule through use of a calibration factor and the sample concentration is provided as an output. The signal source emits radiation at a signal wavelength which is coincident with an absorption band of the chosen molecule while the reference source emits radiation at a reference wavelength which is neutral and not coincident with the absorption band and N is a preselected frequency which is sufficiently fast so that a given molecule of the chosen molecule will not pass in and out of the sample space within the preselected frequency.

The present invention is specifically directed to detection of glucose in blood when the frequency of N Hz is 10 KHz or greater with a duty factor of at least 10%, the signal beam has a signal beam center wavelength of 1,150 nm (1.150µ) and the reference beam has a center wavelength of 1,064 nm (1.064µ).

Accordingly, it is an object of the present invention to provide an improved system and process for scattering noise reduction in the measurement of glucose molecules in blood via NDIR.

This and further objects and advantages will be apparent to those skilled in the art in connection with the figures and the detailed description of the invention set forth below.

DETAILED DESCRIPTION OF THE INVENTION

Figure 1:
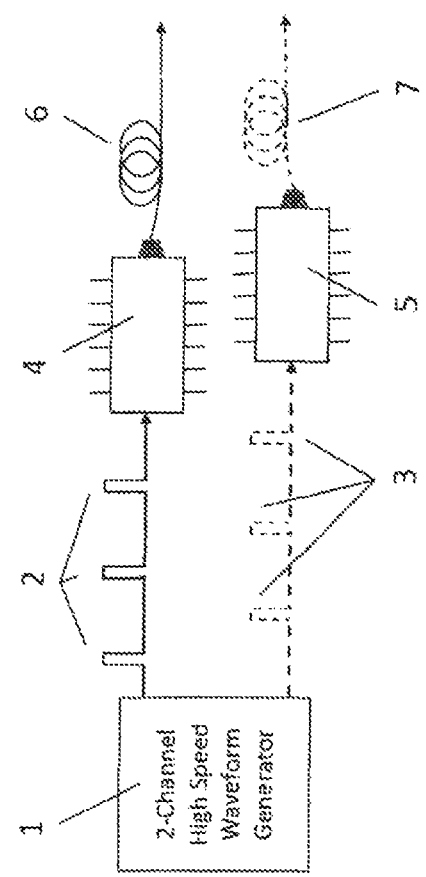
FIG. 1 illustrates how a Signal diode laser and the Reference diode laser are driven alternately and successively by a high speed waveform generator.

An NDIR sensor used to detect molecules in a gaseous phase typically utilizes an infrared source which sends radiation through a sample chamber to a detector which has a spectral filter that passes only radiation which coincides with the absorption band of the gas to be detected. The noise sources of such an NDIR sensor come mainly from the source, the detector and the temperature of the sensor environment.

Traditional NDIR technique uses a double beam configuration to reduce noise. A first channel, called a signal channel, uses an absorption wavelength chosen to detect a target gas and a first detector with a first filter coincident with the absorption of the target gas. A second channel, called a reference channel, uses a neutral wavelength (at which the target gas does not absorb) located close to the absorption wavelength with a second detector with a second filter which is in no way coincident with the absorption of the target gas. Because there are two different detectors, with radiation emanating from the same source, the signal and reference channels have two difference beam paths. The theory is that the signal channel is equally affected by all non-gas phenomena which might introduce noise as the signal channel, so by taking the ratio of the outputs of the two channels, namely the signal and reference channels, one can minimize all the noise-causing factors inevitably present in the sensor. So, ideally, only the presence of the target gas in the optical path will affect the ratio. The reason why the double beam configuration works so well in noise reduction is because particles in a gas phase are very well separated from one another with lots of space between them. Gas molecules typically move around very fast and have a molecular speed in the neighborhood of ~500 m/s. Consequently, at any particular instinct, only a very small number of molecules (including those that are targeted for detection) find themselves in between the source and the detectors. It is because of this particular particle environment that extraneous noise due to unwanted scattering is found to be very small and can be neglected when compared with other traditional noise sources.

If one wishes to use NDIR to detect molecules in liquid, a new source of noise will be introduced, namely, via scattering due to the difference between molecular densities in a gas phase versus that in a liquid phase. Whereas the scattering of source radiation by molecules lying between the source and the detectors is not a significant source of noise in a gaseous medium due to the large amount of free space between molecules, it can become a significant source of noise in a liquid phase where free space between molecules is greatly reduced.

Because of the different particle environment prevailing in the gas and liquid phases, the NDIR absorption technique for the detection of particles works well in the gas phase but not in the liquid phase. In order to solve this problem, the present invention takes an unprecedented approach to come up with a method and apparatus that makes the NDIR absorption technique work in the liquid phase very much like in the gas phase. The same double beam configuration of the traditional NDIR absorption technique is followed which includes the use of a second channel operating at a neutral wavelength just off that of the signal channel. By processing the ratio of the signal outputs from the two channels, namely the signal and the reference, some of the error-causing factors affecting the performance of the sensor will be eliminated, as expected, just as they are similarly eliminated when using the same technique in a gas phase. The additional and unique feature of the present method is to provide a sensor hardware configuration in which both the signal and the reference beams encounter almost exactly the same particle environment during measurement. This is accomplished by executing the following four steps.

Step one is to operate the signal beam and the reference beam separately, each with its own pulsed source. Furthermore, the sources of both beams are pulsed at the same and a very high frequency rate typically greater than 10 KHz with a duty factor around 20-25%. Because of this high pulse frequency requirement, only semiconductor LED and/or diode laser sources will be satisfactory.

Step two is to time the outputs of the signal and reference sources in such a way so that they are turned on alternately and sequentially one at a time, and, in an especially preferred embodiment, separated by no more than one-half of their pulsing period in time. Furthermore, the outputs of these two sources are optically combined via a multiplexer or other means that performs the same function so that both the signal and the reference beams physically traverse the same space of liquid matrix before being detected by a single infrared detector. The detector is required to have a response time fast enough to adequately generate the correct signal outputs from the rapidly incident radiation pulses from the signal and the reference beams.

Step three is to choose the wavelength of the signal and the reference channels. The choice of the wavelength for the signal channel has to be coincident with the absorption band of the target particle to be measured. The wavelength for the reference channel has to be neutral but just off the absorption and as close to it as possible but in no way coincident with it. This way of choosing the wavelength for the reference channel has to do with making sure that the same particle environment for purposes of scattering is almost the same for both the signal beam and the reference beam (if their wavelengths are almost the same). This is because of the fact that elastic scattering is a function of the wavelengths of the radiation in the incident beams.

Step four is processing the data received by the detector and explains how the calibration procedures are carried out in order to obtain the concentration level of the particles in the liquid. When the Signal beam and the Reference beam are alternately and successively pulsed at N Hz ($N>10^4$), a ratio value "R" is calculated for each generated Signal channel output and the corresponding Reference channel output, namely R=Signal/Reference. At the pulse rate of N Hz, there will be N such ratio values generated every second. For a preselected pulsing time period of "t", where "t" is in seconds, there will be N×"t" ratio values generated. The average value of R over this time period "t", namely $R_{ave}(t)$, is calibrated against the concentration of particles in the liquid. Thus the value of $R_{ave}(t)$ obtained by using a signal processing technique for analyzing the detector outputs yields the concentration level of the particles in the liquid.

The present invention takes advantage of the fact that although the density of molecules in the liquid phase is very high, the velocity of the molecules moving about in it is very slow, typically ~5 mm/sec. Thus, assuming that the cross-sectional area of the sampling matrix is of the order of a few $mm^2$, the time taken for molecules to move in and out of the sampling area many times is of the order of hundreds of milliseconds. Accordingly, if the measurement time between the Signal beam and the Reference beam is of the order of a few tenths of a millisecond, the particle environment traversed by both beams during the measurement can be considered as almost unchanged or substantially identical. In other words, since the particle environment for the Signal and the Reference channels during their respective measurement hardly changes when steps 1-4 described above for the liquid phase are executed, the phenomena of unwanted scattering should stay pretty much the same for both beams, with a resultant significant reduction and suppression of noise attributable to scattering arising from a liquid phase sampling environment.

FIGS. 1-4 schematically depict a specially designed apparatus that is used to implement the method of rendering the NDIR absorption technique workable in the liquid phase by suppressing unwanted scattering noise due to the presence of a large number of mobile particles in the liquid matrix between the source and the detector.

As shown in FIG. 1, a 2-channel high speed waveform generator 1 (>10 KHz) is employed to generate alternately and successively voltage pulses 2 and 3 to drive, respectively, Signal diode laser 4 and Reference diode laser 5. As shown in FIG. 1, the outputs of both diode laser 4 and diode laser 5 are interfaced respectively to optical fibers 6 and 7. The narrow spectral output of Signal diode laser 4 is selected to coincide with the absorption band of the target particle to be detected in the liquid matrix. But the narrow spectral output of Reference diode laser 5 is selected to be off but close to the absorption band of the target particle in the liquid matrix to be detected.

Figure 2:
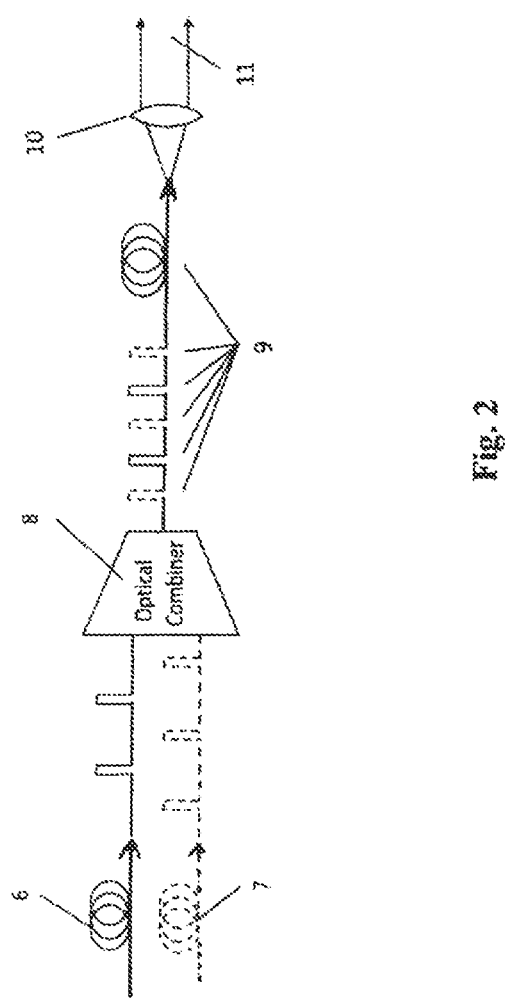
FIG. 2 illustrates how the outputs of the Signal diode laser and the Reference diode laser are combined into a single radiation beam alternately and successively representing both diode lasers via the use of an optical multiplexer.

FIG. 2 illustrates how outputs of the Signal laser beam 4 and Reference laser beam 5 are spatially combined into a single radiation beam before being focused onto the infrared detector. As shown in FIG. 2, output of the Signal laser beam 6 and output of the Reference laser beam 7 are combined in an optical multiplexer 8 to form a single radiation beam 9 before being collimated into a parallel beam 10 by collimating lens 11.

Figure 3:
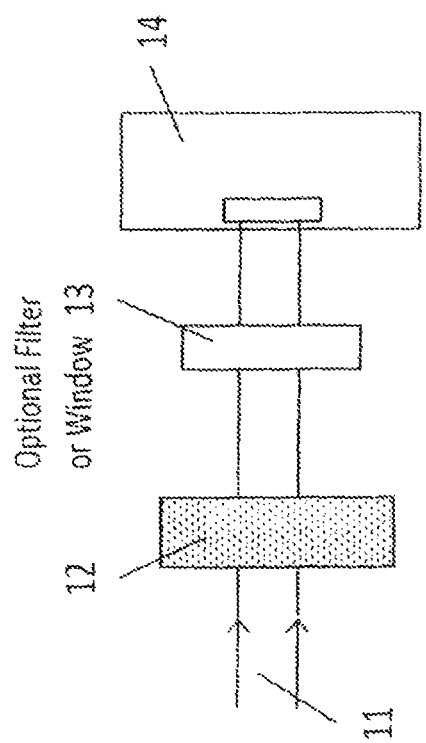
FIG. 3 illustrates the trajectory of the combined Signal and Reference diode laser beam to the infrared detector after passing through the sample chamber containing the liquid matrix and additional optional optical elements.

FIG. 3 illustrates how parallel radiation beam 10 (see FIG. 2) finds its way to the infrared detector. As shown in FIG. 3, single parallel beam 10 (which actually comprises both Signal laser beam 6 and Reference laser beam 7 being turned on alternately and successively by the 2-channel high speed waveform generator 1 of FIG. 1) first traverses sample chamber 12 containing the liquid matrix before being incident onto a TE-cooled infrared detector 14 after passing through an optional filter or window 13 for noise reduction (if needed).

Figure 4:
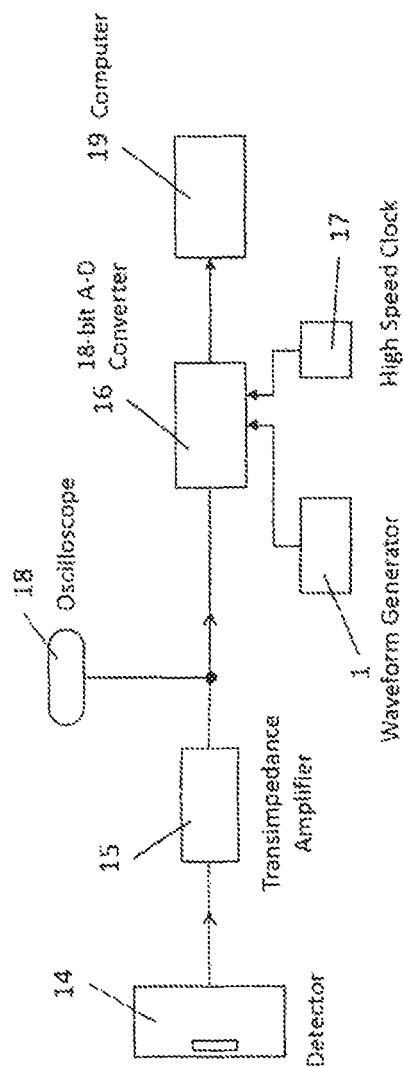
FIG. 4 illustrates the steps for transforming the analog infrared detector signal into digital data before inputting them into the computer for final data processing and analysis.

For signal processing as illustrated in FIG. 4, output of infrared detector 14 is first fed into a transimpedance amplifier 15 the output of which is inputted to an 18-bit Analog-to-Digital converter 16 triggered by waveform generator 1 (see FIG. 1) and a high speed clock 17. The analog signal can be monitored by an oscilloscope 18 before the digital signal is fed into a computer 19 for data analysis. Calculated ratio values are cross referenced to known compound concentration values. These compound concentration values can be reported individually to an output device such as a flat panel display. As values are collected over time, they can be plotted in a graphical format to illustrate trends over time. Running compound concentration values can be averaged over time, as one example, for smoother data tracking. Data output 20 can be sent from the detector electronics by wired or wireless interfaces such as Bluetooth or WiFi standards to external devices.

Figure 5:
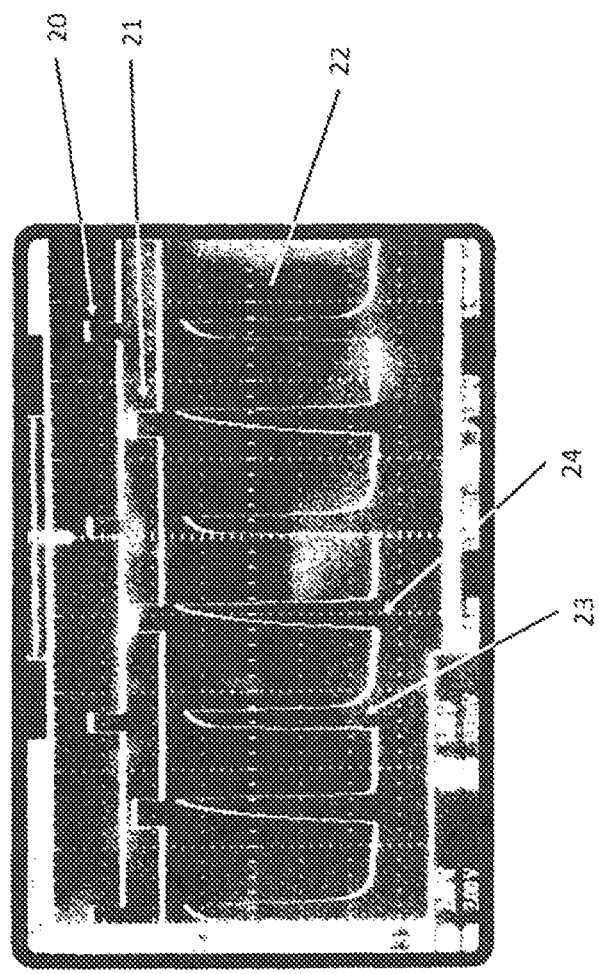
FIG. 5 illustrates the analog voltage outputs for driving the Signal and Reference diode lasers and the analog detector output for the combined laser beam prior to digitization.

FIG. 5 portrays the analog output as monitored by oscilloscope 18 (see FIG. 4). As shown in FIG. 5, the top two traces 20 and 21 of the oscilloscope display are voltage pulses 2 and 3 generated alternately and successively by high speed waveform generator 1 for driving respectively Signal diode laser 4 and Reference diode laser 5 (see FIG. 1). The bottom trace 22 of the oscilloscope display shows alternately the analog outputs of Signal laser beam 23 and Reference laser beam 24 from infrared detector 14 (see FIG. 3).

The processing of the digital data received by the computer from the infrared detector after initial data manipulation goes as follows. When both the Signal and Reference channels are pulsed at N Hz (N>$10^4$) for a measurement time period "t", where "t" is in seconds, there will be N×t Signal channel outputs and an equal number of Reference channel outputs generated by the infrared detector. A ratio value "R" is calculated for each generated Signal channel output and the corresponding Reference channel output, namely R=Signal output/Reference output. For the N×t ratio values of R calculated over the measurement time period 't', an average, namely $R_{ave}(t)$, is calculated. The calculated value of $R_{ave}(t)$ represents the measurement signal for the average concentration level of particles in the liquid in the time period "t". It is important to note that the signal to noise (S/N) for the measurement value of $R_{ave}(t)$ versus the average concentration level of particles in the liquid is a function of the value of the preselected time period "t". The longer the measurement time period "t", the noise in the value of $R_{ave}(t)$ is smaller as there are more collected data to be averaged for the measurement value of it.

Figure 6:
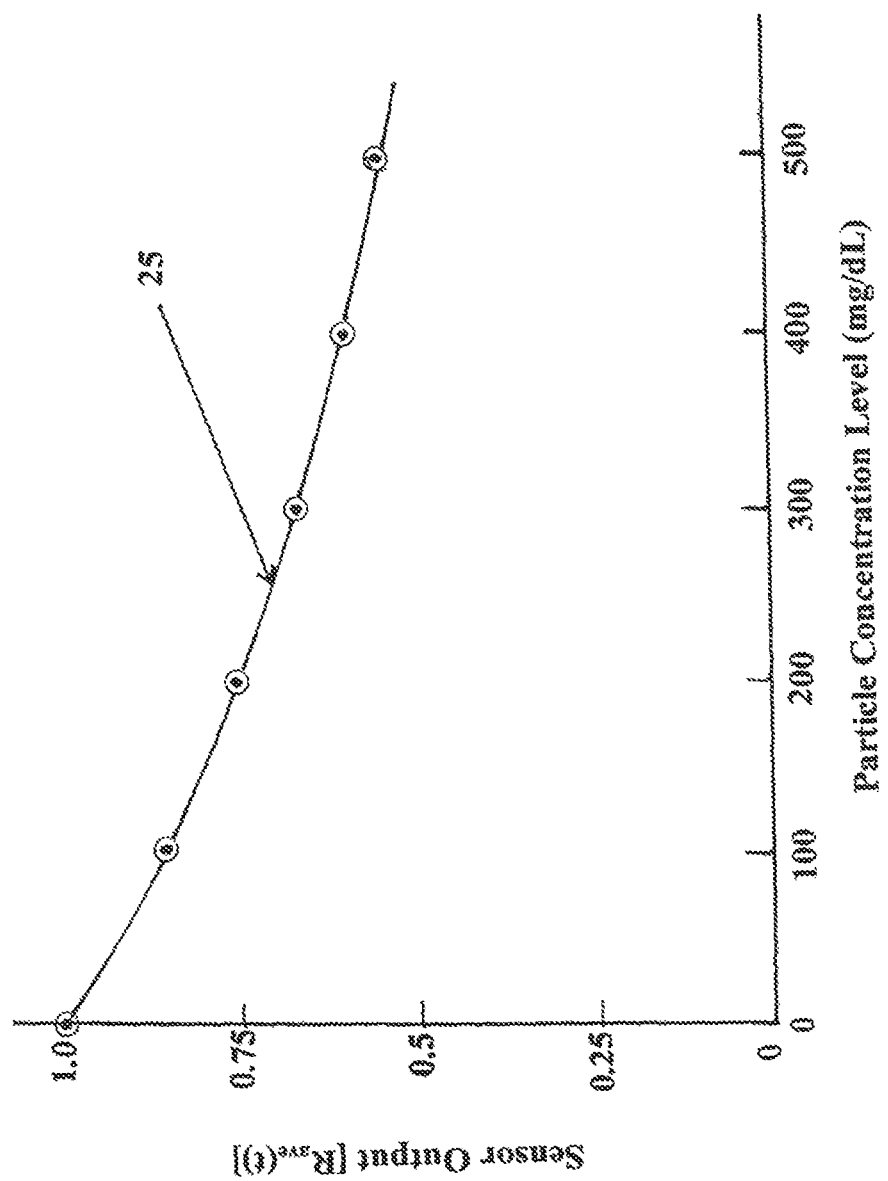
FIG. 6 illustrates a calibration curve for an NDIR liquid sensor depicting the sensor output ratio $R_{ave}(t)$ for the Signal and the Reference beams as a function of the particle concentration levels in liquid measured in milligram per 100 c.c. (mg/dL).

FIG. 6 shows graph 25 depicting the value of $R_{ave}(t)$ for a particular preselected measurement time period "t" as a function of the averaged particle concentration level "D" in the liquid measured in milligram per 100 cc (mg/dL). As can be seen in FIG. 6, the graph 25 is in essence the calibration curve of the particle concentration level for the NDIR liquid sensor. Such a calibration curve is attained by first selecting a liquid wherein different concentrations of particular particles in it are to be determined. Samples possessing different particle concentration levels in the liquid are then prepared. A measurement time period "t" is next selected for the calibration. By executing the four steps elucidated earlier for the measurement procedure, the values of $R_{ave}(t)$ are determined for each sample concentration in the liquid. The graph 25 as depicted in FIG. 6 portrays the value of $R_{ave}(t)$ as a function of the concentration levels of particles in the liquid with a preselected measurement time period "t".

The principles set forth so far will now be illustrated in greater detail by reference to a specific use of the inventive process and system for determining blood glucose concentration levels. In the near infrared (NIR) spectral region, glucose has an overtone absorption band located at 1,150 nm which can be used as the center wavelength for the signal beam. This absorption band is desirable because it has a water absorption coefficient of no greater than ~1.0 $cm^{-1}$, which is especially preferred, as it helps to minimize effects created by water absorption. A reference beam wavelength of 1,064 nm, where there is no glucose molecule absorption, can be used as the center wavelength for the reference beam. Therefore, by using a pulse frequency of 10 KHz or more, 1,150 nm as the center wavelength for the signal beam with a relatively narrow bandwidth (+/−a few nm) and 1,060 nm as the center wavelength for the reference beam with also a relatively narrow bandwidth, one is able to apply the principles of the present invention to detection of glucose molecules in blood. An apparatus using such principles can be designed so that the sample area is a small portion of a human body containing blood, such as the webbing of a finger or an ear lobe, which is placed (or clamped) between the pulsed beam and the detector.

While the invention has been described herein with reference to a preferred embodiment, this embodiment has been presented by way of example only, and not to limit the scope of the invention. Additional embodiments thereof will be obvious to those skilled in the art having the benefit of this detailed description. Further modifications are also possible in alternative embodiments without departing from the inventive concept.

What is claimed is:

1. A process for determining a blood glucose concentration in a human sampling matrix, comprising:
    alternately and sequentially pulsing infrared radiation from a signal source and a reference source at a frequency of N Hz into a multiplexer and collimating radiation leaving the multiplexer into a pulsed beam which is directed through the human sampling matrix;
    detecting infrared radiation by a detector as a pulsed signal and reference channel output from the pulsed beam after it passes through the human sampling matrix;
    using signal processing to obtain an average ratio value of $R_{ave}(t)$ for a preselected period of time ("t") from the pulsed signal and reference channel output, where $R_{ave}(t)$=signal channel/reference channel output for the preselected period of time;
    using electronics to calculate the blood glucose concentration by use of $R_{ave}(t)$ and a calibration factor; and
    providing the blood glucose concentration as an output from said electronics;

wherein the signal source emits radiation at a signal wavelength which is coincident with an absorption band of glucose while the reference beam emits radiation at a reference wavelength which is neutral and not coincident with the absorption band;

wherein N is a preselected frequency which is sufficiently fast so that a given molecule of the chosen molecule will not pass in and out of the sample space within the preselected frequency; and wherein the signal wavelength has a water absorption coefficient no greater than ~1.0 cm$^{-1}$.

2. The process of claim 1 wherein the frequency of N Hz is 10 KHz or greater with a duty factor of at least 10%.

3. The process of claim 1 wherein the signal beam has a signal beam center wavelength of 1,150 nm (1.150μ) and the reference beam has a center wavelength of 1,064 nm (1.064μ).

4. A system for determining a blood glucose concentration in a human sampling matrix, comprising:
- a multiplexer;
- a signal source configured to emit pulsed infrared radiation into the multiplexer at a signal wavelength which is coincident with an absorption band of glucose at a frequency of N Hz;
- a reference source configured to emit pulsed infrared radiation into the multiplexer at a reference wavelength which is neutral and not coincident with the absorption band at the frequency of N Hz;
- a collimator configured to collimate radiation leaving the multiplexer into a pulsed beam which is directed through the human sampling matrix;
- a detector which generates a pulsed signal and reference output from the pulsed beam after it passes through the human sampling matrix; and
- signal processing electronics which provide the blood glucose concentration as an output obtained by using signal processing to obtain an average ratio value of $R_{ave}(t)$ for a preselected period of time ("t") from the pulsed signal and reference channel output, where $R_{ave}(t)$=signal channel output/reference channel output for the preselected period of time, and said signal processing electronics use $R_{ave}(t)$ and a calibration factor to calculate the blood glucose concentration;

wherein the frequency of N Hz is 10 KHz or greater with a duty factor of at least 10%, the signal beam has a signal beam center wavelength of 1,150 nm (1.150μ) and the reference beam has a center wavelength of 1,064 nm (1.064μ).

\* \* \* \* \*